United States Patent [19]
Fleer et al.

[11] 4,107,846
[45] Aug. 22, 1978

[54] DEVICE FOR SUPPLYING COOLING AGENTS TO A DENTAL INSTRUMENT OF A HANDPIECE

[75] Inventors: Ernst-Otto Fleer, Bensheim-Auerbach; Erich Heubeck, Bensheim, both of Germany

[73] Assignee: Siemens Aktiengesellschaft, Berlin & Munich, Germany

[21] Appl. No.: 720,051

[22] Filed: Sep. 2, 1976

[30] Foreign Application Priority Data

Sep. 25, 1975 [DE] Fed. Rep. of Germany ....... 2542826

[51] Int. Cl.² ............................................. A61C 1/10
[52] U.S. Cl. ............................................. 32/27; 32/58
[58] Field of Search ................................. 32/26, 27, 28

[56] References Cited
U.S. PATENT DOCUMENTS

| 2,532,054 | 11/1950 | Broussard et al. | 32/28 |
| 2,557,377 | 6/1951 | Ganz | 32/28 |

*Primary Examiner*—Robert Peshock
*Attorney, Agent, or Firm*—Hill, Gross, Simpson, Van Santen, Steadman, Chiara & Simpson

[57] ABSTRACT

An improved dental handpiece having a device for supplying a cooling agent to a driven dental instument supported in a head portion of a handle section which is removably mounted on a center section of a handpiece characterized by the device for supplying fluid supplying fluid to a first group of ports which are connectable with an external conduit of a first type of handle section for delivering fluid to the dental instrument and a second group of ports arranged to supply fluid to internal fluid passages of a second type of handle section in which the cooling conduits are incorporated therein and a device for preventing flow from one group of ports so that hand sections having either external cooling conduits or incorporated internal conduits for cooling fluid can both be utilized with the handpiece. In the embodiments of the improvement, the means for preventing flow may either be various valve arrangements, or specially designed plugs and fluid connections.

4 Claims, 15 Drawing Figures

DEVICE FOR SUPPLYING COOLING AGENTS TO A DENTAL INSTRUMENT OF A HANDPIECE

BACKGROUND OF THE INVENTION

Field of the Invention

The present invention is directed to a device for supplying cooling agents to a dental instrument supported and driven by a handpiece.

Prior Art

Dental handpieces which utilize a drive means comprising either an air or electric motor are known. In order to cool the location under preparation, a cooling agent is conveyed in an exposed flexible cooling agent supply hose or tube which extends outside or on the exterior of the handpiece to a head section that supports the dental instrument. The hose or tube is often provided with a certain amount of excess length so that the handle section of the handpiece can be rotated relative to a center section or portion, which contains the drive means, without over-extending the hose or tube.

A disadvantage with such an arrangement is that during each removal or replacement of a handle section from and on the center section of the handpiece, the cooling agent hose must be separated from a connecting piece and wound up on the handle section. A further disadvantage is that the exposed cooling agent supply hose may restrict the free rotatability of the handle section relative to the center section of the handpiece and that the hose often interferes with the manipulation of the handpiece during its use. A final disadvantage is that the cooling agent supply hose or tube can inadvertently become snagged on adjacent handpieces or on the storage rack.

It has already been proposed that the cooling agent lines be incorporated in the interior of a handpiece so that they are provided on the center section and coupled into a handle section which is removably mounted on the center section. This is accomplished in such a manner that when the handle section is mounted on the center section, the cooling line segments are automatically connected with one another. To some desired extent, the rotatability of the handle section relative to the center section, which is rigidly connected to a cooling agent supply hose, is achieved by the arrangement of corresponding seal ring channels.

If a handpiece is provided for supplying cooling agent to a handle section which has the cooling agent conduits incorporated in the interior thereof, a handle section of a type, which has exposed cooling agent conduits, can only be used therewith if one dispenses with the supply of cooling agent to the head section and dental instrument. However, since only a few types of preparation can be performed without a cooling agent, the interchangeability of different types of handle sections is not practical.

SUMMARY OF THE INVENTION

The present invention is directed to a handpiece wherein it is possible to use either a type of handle section which has an incorporated internal cooling agent conduit or a type of handle section which has an exposed cooling agent supply line or tube without dispensing with the cooling agent at the desired location with either type of handle section. Thus, the object of the present invention is to provide a dental handpiece which may use either type of handle portion and still obtain the desired flow of cooling agents to the area of the dental instrument.

To accomplish these tasks, the present invention is directed to improvement in the device for supplying at least one cooling agent to a dental instrument supported in the head portion of a handpiece, said handpiece having a center section containing a drive means for a dental instrument and having a drive shaft surrounded by an axially extending shank at one end thereof, said center section of an opposite end having a feed channel for a cooling agent connected by a fitting portion to a supply hose for the cooling agent, said handpiece including a detachable handle section having the head portion mounted on one end, said handle section being detachably mounted for rotation relative to the center portion by being telescopically received onto the shank, and said handpiece including means for supplying a cooling agent from the feed channel to a discharge port on the head portion directed at the dental instrument. The improvement comprises said means for selectively supplying fluid to both a first type handle section having an exposed cooling agent conduit extending to the discharge port and a second type of handle section having an incorporated cooling agent supply line extending to the discharge port, said means for supplying including at least one first port and at least one second port, each first port being a peripheral opening on the center portion for receiving a connection to the exposed cooling agent supply conduit of the first type handle section, each second port being an opening disposed on the shank for connection to the incorporated supply line of the second type of handle section, and means for preventing issuance of the cooling agent from each of said first and second ports so that both the first and second types of handle sections can be mounted on the shank and supplied with a cooling agent.

It is essential in terms of this invention that the handpiece contains ports at two different locations for discharging a cooling agent or agents so that one group of ports is designed for connection to a flexible exposed cooling agent hose and the other group of ports is designed for connection to an incorporated cooling agent line of a second type of handle section.

Various embodiments of the invention and the advantages thereof are explained and described in the following portions of the specification and illustrated in the drawings.

DESCRIPTION OF THE PREFERRED EMBODIMENTS

Figure 1:
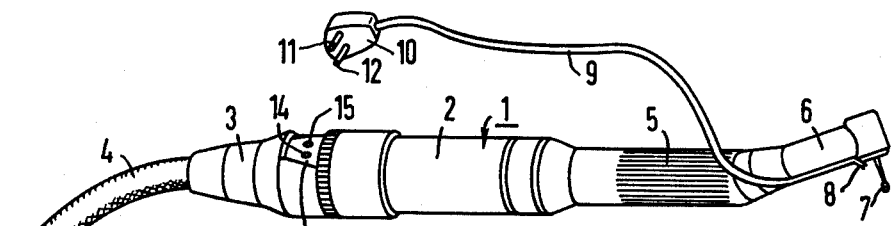
FIG. 1 is a perspective view of a dental handpiece in accordance with the present invention having a handle section of the first type with an exposed cooling agent supply conduit.

The principles of the present invention are particularly useful when incorporated in dental handpiece generally indicated at 1 in FIG. 1. The handpiece 1 has a center section or portion 2 in which a non-illustrated drive means, for example a micro-motor drive, is housed. One end of the center section 2 is connected to a supply hose 4 by a connecting fitting portion 3. The supply hose 4 contains an energy supply line for the drive means as well as at least one cooling agent line for cooling a location under preparation by a dental instrument 7 of the handpiece 1.

A first type of handle section 5, which has a head portion or section 6, is mounted on the other end of the center section 2 for rotation about a longitudinal axis of the handpiece 1. The dental instrument 7, which is driven by the drive means of the center section 2 through a drive train which is contained in the handle section 5, is rotatably supported on the free end of the head section 6. A short piece of cylindrical tubing or pipe 8 is mounted on the external surface of the head section 6 and has an open end or outlet port which forms a discharge nozzle or port that is directed toward the dental instrument 7. A flexible hose 9 is inserted on the other end of the cylindrical tube 8 and the free end of the hose line is connected with a distributor member 10.

The distributor member 10 has two tubular prongs 11 and 12, which, when the distributor member 10 is placed on a corresponding connecting section 13 adjacent the center section 2 such as on the fitting portion 3, are received in first ports 14 and 15. Air may be discharged from one of the two ports 14 and 15 and water from the other port so that when the distributor member has its prongs 11 and 12 inserted in the ports 14 and 15, it will receive both air and water which will be conveyed by the common conduit or hose 9 to the nozzle formed on the tube 8 at the head section 6. Thus, air and water are mixed together with one another in the distributor member 10 and then supplied to the head section 6 as an air-water mixture for spraying at the area being prepared by the dental instrument 7. Of course, air and water can also be supplied to the head section separately via two flexible hose lines or can be combined prior to reaching the distributor member 10 in which case the distributor member 10 will contain only one tubular prong for connecting the distributor member to the source of the air and water mixture.

Figure 2:
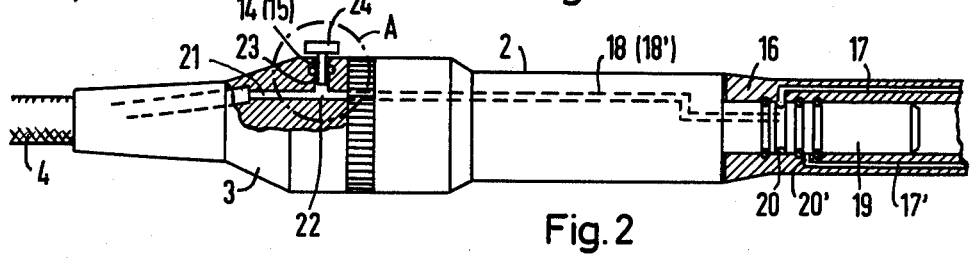
FIG. 2 is a side elevation with portions broken away for purposes of illustration of a handpiece in accordance with the present invention with a second type of handle section having incorporated interior cooling passageways or conduits.

In FIG. 2, the center section 2 is illustrated as receiving a handle section 16, which is of the second type and which only a portion adjacent the center section 2 is illustrated. In addition for simplicity of illustration, only a single path or passageway for a single cooling agent is illustrated. The path or passageway for the other cooling agent would extend parallel to the illustrated passageway and, if necessary, throttle valves may be arranged in either one of the passageways or in both conduits or passageways.

The center section 2 has an axially extending shank 9, which surrounds a drive shaft for the motor. The handle portion 16 of the second type is rotatably mounted on the center section 2 by being telescopically received on the shank 19 and the handle portion will have a drive train (not illustrated) which will be connected to the non-illustrated drive shaft which is surrounded by the shank 19. The handle section 16 is of the second type which has internal or incorporated cooling passageways which are illustrated as conduits 17 and 17'. The conduits 17 and 17' are connected to cooling passageways or segments 18 of the center section 2 by ring channels 20 and 20', respectively, which are in communication with the second ports of the cooling agent supply means of the handpiece 1. As mentioned above, each of the cooling agents supplied by the hose 4 is received by a separate feed channel 21 which is illustrated as being located in the fitting 3. Passageway or supply lines 18 and 18', respectively, are in communication with the respective feed channel such as 21 and the passageway 18 has a branch 22 having a radial directed channel or passage 23 which extends to a peripheral opening of one of the first ports such as 14.

In the embodiment illustrated in FIGS. 1 and 2, the means for preventing flow from one of the first and second ports includes a plug 24 which has a solid prong for each first port. The plug 24 has each of its prongs inserted in the peripheral opening of the first port and into sealing engagement with an O-ring disposed in the channel 23. Thus, fluid in the feed channel 21 will be conveyed by the passageway such as 18 to the second port, into the groove 20 and to the internal passage or conduit 17 in the handle section 16. It is noted that the solid prong of the plug 24 has a selected length so that it does not extend into the channel or passage 23 to such an extent as to block flow to the passage 18.

When using a first type of handle section such as handle section 5, the tubular prongs 11 inserted in the ports such as 14 will extend into the channel and receive the fluid. The handle portion 5 when received on the shank 19 will block flow from the ring channels such as 20 and thus prevent any flow from the second ports.

While each of the embodiments illustrated in FIGS. 3–10 may contain passageways for separately conveying two different cooling agents, for the purpose of simplifying the illustration, one single passageway for a single agent is illustrated. It should be understood that in each embodiment, a second identical passageway system can be included.

Figure 3A:
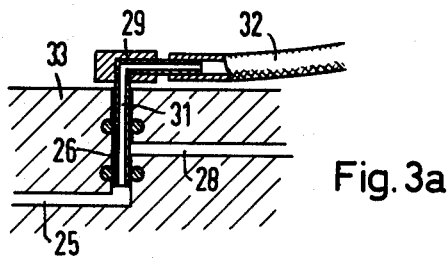
FIGS. 3a and 3b are partial cross sections taken at a circle indicated at A in FIG. 2 and illustrating an embodiment of the means for preventing flow to different ports.
Figure 3B:
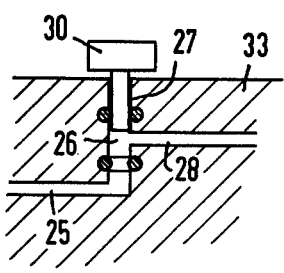

In a first embodiment of the invention as illustrated in FIGS. 3a and 3b, the blocking of the ports occurs at a single position. As illustrated, a connecting portion 33 has a feed channel 25 which is connected to the feed channel 21 illustrated in FIG. 2. The channel 25 has a radial segment or passageway 27 from which a second passageway or channel 28 branches off at point 26 and extends parallel to the axis of this center section and extends to the second port at the sealed grooves such as 20 on the shank 19. As noted, the channel or passage 28 is disposed radially outward of the position of the segment or channel 25. The passageway 27 on each side of the point 26 is provided with seals such as O-rings. Thus, when a tubular prong 31 of a distributor element or connecting link 29 is inserted radially into the passageway or channel 27, the tubular prong 31 by engaging the sealing rings blocks flow to the second passageway 28. The other end of the tubular prong 31 receives the tube or conduit such as 32 which is an external or exposed fluid conduit for the first type of handle section. When using a second type handle section such as 16, a closing or dummy plug 30 (FIG. 3b) having a solid prong is inserted in the passageway 27. As illustrated, the length of the prong of the plug 30 is selected so that it engages at least one sealing ring to block flow through the first port but does not block flow to the passageway 28.

Figure 4A:
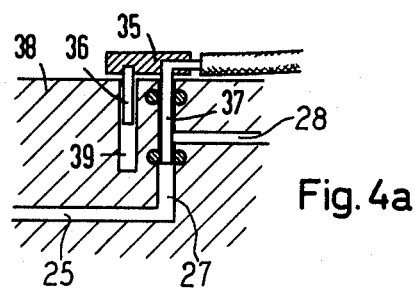
FIGS. 4a and 4b are partial cross sections of the area indicated by the broken line circle A of FIG. 2 and illustrate a second embodiment of the means for preventing flow to the various ports.
Figure 4B:
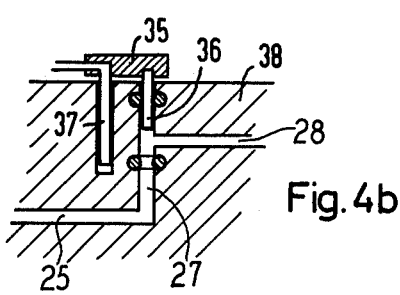

In the embodiment illustrated in FIGS. 4a and 4b, a center section 38 is provided with conduits 25, 27 and 28 as in the previously described embodiment. In this embodiment, a distributor member or element 35 on one side has both a solid prong 36 and a tubular hollow prong 37 for each of the first ports. The center member 38 is provided with a radially extending bore 37 whose spacing from the passage 27 corresponds to the spacing between the solid prong 36 and the corresponding tubular prong 37.

When using a handle section of the first type, the distributor member 35 is inserted as illustrated in FIG. 4a with the hollow or tubular prong 37 in the channel 27 and the solid prong 36 in the radial bore 39. Fluid flow into the passageway 28 is blocked by the tubular member 37 which conveys the fluid to a tube such as 32 which extends to the discharge nozzle on the first type of handle section. When changing handle sections and going to a handle section of the second type such as handle section 16, the tube 32 is disconnected from the element 35. The element 35 is then removed, rotated 180° and then reinserted as illustrated in FIG. 4b with the tubular prong 37 extending into the bore 39 and the solid prong 36 extending into the passageway 27 to block flow from the first port without interferring with flow through the second passageway 28 to the second port.

Figure 5A:
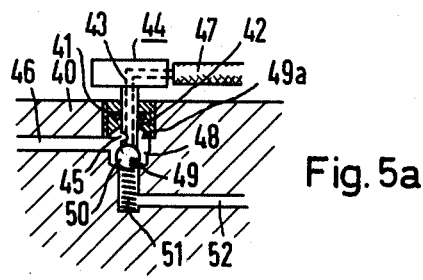
FIGS. 5a and 5b are partial cross sections of the area A of FIG. 2 and illustrate a third embodiment of the means for selectively preventing flow to the various ports.
Figure 5B:
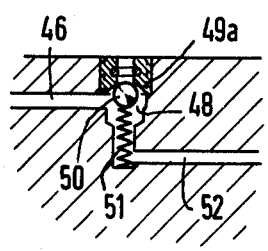

In the third embodiments illustrated in FIGS. 5a and 5b, a center section 40 has a radially extending bore threadably receiving an insert 41. The insert 41 is provided with a radially extending channel or passage 42 which is provided with a seal member and will receive a hollow or tubular prong 43 of a plug or distributor element 44. The hollow tubular prong 43 is closed at its end but provided with a transverse passage or bore 45 and has its opposite end connected to a cooling agent hose or conduit 47, which corresponds to the hose 9 of FIG. 1.

The insert 41 with the radial bore in the section 40 forms a chamber 48 which is in communication with a conduit or passage 46 that will extend to or is in communication with a feed channel such as 21. The chamber 48 has valve seats 49 and 49a with the valve seat 49 coacting with a valve member such as the ball 50 to prevent flow into a second passageway or conduit 52 which leads to the second ports on the shank 19. The valve seat 49a cooperates with the valve member or the ball 50 to prevent flow through the passage 42. As illustrated in FIG. 5a, the insertion of the hollow prong 43 holds the ball 50 on the valve seat 49 to prevent flow into the second passageway 52 and thus to the second port and the fluid will flow through the transverse bore 45 to the tube 47. With the removal of the distributor element 44, the ball or valve member 50 is resiliently urged or biased by a spring 51 against the valve seat 49a to open flow to the second passageway 52 extending to the second ports and to prevent flow to the passageway 42 of the insert 41 and the first ports (FIG. 5b).

When using a second type of handle section having an incorporated internal cooling agent conduit such as handle section 16. This embodiment does not require a dummy plug to close the first ports. If the distributor element such as 44 is a component element of the first type of handle section with the exposed cooling agent conduit, this embodiment is also advantageous. When assemblying a handle section of the first type onto the shank, and with the insertion of the hollow prong 43 in the passage 42, the tubular prong will move the valve member 50 against the seat 49 to restrict and prevent flow into the second passageway 52 and to place the passageway 46 into communication with the exposed conduit 47. Thus, insertion and removal of the distributor element 44 will determine which of the two different ports will receive the cooling fluid.

Figure 6A:
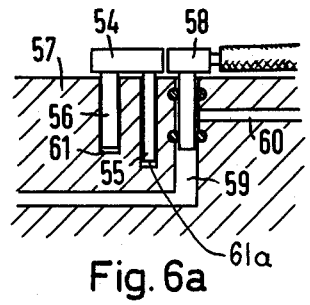
FIGS. 6a and 6b are partial cross sections of the area of circle A of FIG. 2 and illustrate a fourth embodiment of the means for preventing flow to the different ports.
Figure 6B:
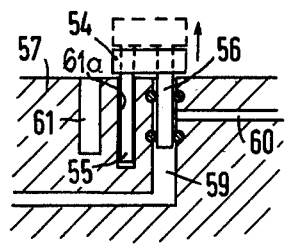

In the fourth embodiment illustrated in FIGS. 6a and 6b, the plug member such as 54 is provided with a guide pin 55 and a closing pin or solid prong 56. A center section 57 is provided with corresponding bores 61 and 61a for receiving the closing pin 56 and the guide pin 55, respectively. Since a plug-in connector 58 is usually provided on the end of the exposed conduit or tube of a handle section of the first type, removal of the first type handle section causes the removal of the element 58 from a radial bore 59 that interconnects a feed channel to the first port and also to a second passageway 60 that extends to the second port. To close the first port, the element 54 is moved to withdraw the closing pin 56 from the bore 61 and then rotate 180° so that the closing pin 56 can be inserted into the opening of the first port and the passage 59 (see FIG. 6b). Depending on how far the pin 56 is inserted into the passage 59, the pin 56 will determine whether the passageway 59 will remain in fluid communication with the second passageway 60 leading to the second port. As illustrated in broken lines in FIG. 6b, the position of the pin 56 allows fluid flow into the second passage 60. When the member 54 is pushed to the position illustrated in bold lines, the pin 56 blocks fluid flow to both passageways and prevents fluid flow to either of the ports. This feature of the embodiment is desirable when using a handpiece in a dental preparation which does not require any cooling agent. Thus, an unintentional issuance of a cooling agent from the head section due to an inadvertent actuation of the foot control is prevented.

In the above described embodiments, the cooling agent line paths or passageways for providing fluid to either type of handle section are positioned virtually parallel to one another so that a branch is present and means are provided for connecting one or the other of the passageways to the source of cooling agent depending upon need. The connection can be made either voluntarily or automatically upon the connection of one or both of the cooling agent supply conduits. In the next embodiment the line passageways are in series with one another so that one segment of a passageway can be connected to the other passageway via a bridging or distributor member.

Figure 7:
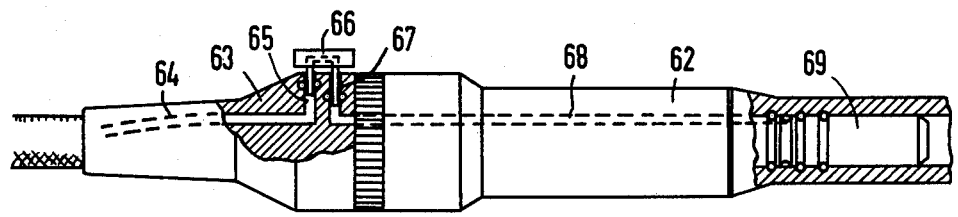
FIG. 7 is a side elevational view with portions broken away for purposes of illustration of a handpiece in accordance with the present invention illustrating a fifth embodiment of the invention.

In the embodiment illustrated in FIG. 7, a passageway 65 is arranged in the fitting 63 of a center section such as 62. The passageway 65 is connected to a supply channel 64 which will receive fluid from the hose such as 4 and the channel or passageway 65 extends radially to a peripheral opening forming the first port. A bridging member 66 is provided with a U-shaped tubular member which has one leg received in a radial extending segment 67 that is in fluid communication with a second passageway 68 that extends to the second port on a shank 69.

As illustrated in FIG. 7, the bridging element 66 communicates or connects flow from the passage 64 to the second port and this is the desired situation when using the second type of handle section. When using the first type of handle section which has the exposed fluid supply conduit, the bridging element 66 is removed and replaced by a plug having a hollow prong which is received in the portion 65. With the replacement of the bridging element 66 with a plug having a hollow prong, the fluid will flow from the passage 65 through the exposed tube to the discharge nozzle of the first type of handle section. Also, the second passage 68 is disconnected from the source of cooling fluid.

Figure 8:
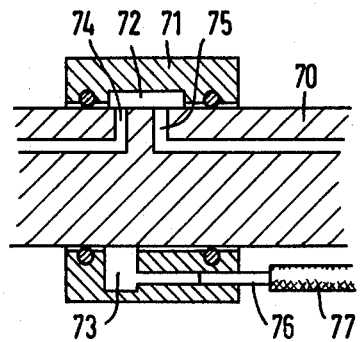
FIG. 8 is a cross-sectional view of a portion of a handpiece illustrating a sixth embodiment of the present invention.

In the embodiment illustrated in FIG. 8, a center section 70 receives a rotatable adjustment ring 71 which is a switch over valve. As illustrated, the center section is provided with a radial extending port such as 74 that is in communication with a source of the cooling fluid. Adjacent the port 74 is a second portion 75 which is in communication with a second passage extending to the second port on the shank. An inner cylindrical surface of the ring section 71 is provided with two chambers 72 and 73 which can be formed by two circumferentially spaced grooves. The chamber 72 has a sufficient width so that the chamber 72 bridges both of the radial directed cooling agent lines such as 74 and 75 in order to form a connection of the source of cooling agent to the second port. The groove 73, however, is provided with a passage which will receive a fitting 76 of an exposed fluid conduit 77 of the first type of handle section. The groove 73 only has a sufficient size to engage only the port of the passage 74. Thus, when the ring 71 is rotated approximately 180° to place the groove 73 over the port 74, fluid from the source of the cooling agent is in communication with the connection 76 and the exposed cooling agent hose or tube 77. While the connecting fitting 76 is illustrated as a tubular member, it can be a connecting plug which is normally provided on the end of the exposed hose such as 77.

Figure 9:
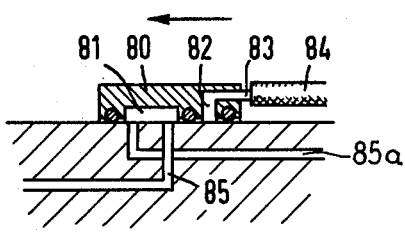
FIG. 9 is a partial cross section of a portion of a handpiece illustrating a seventh embodiment of the present invention.

In the embodiment illustrated in FIG. 9, a ring 80 which is a switch-over valve, is received on the center section and is axially shifted thereon. The device 80 is provided with a chamber 81 which corresponds to the chamber 72 of the embodiment of FIG. 8 and the chamber 82 which corresponds to the chamber 73. The chamber 82 is connected with a connecting piece such as 83 to the corresponding flexible cooling agent supply hose or tube 84 which can be either attached directly on the tube 83 or have a plug which is inserted into the passage receiving the tube 83.

As illustrated in FIG. 9, the member 83 is in a position so the chamber 81 bridges the conduit 85 to a conduit 85a, which is the location desired when using the second type of handle section. When removing the second type of handle section and using a first type, the member 80 is shifted in the direction of the arrow so that the notch or chamber 82 covers only the port of the passage 85, so that the fluid flow will be in communication with the exposed tubes such as 84.

Figure 10:
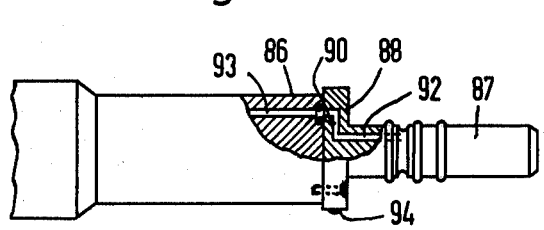
FIGS. 10a and 10b are side elevations with portions broken away for purpose of illustrating a portion of a handpiece illustrating an eighth embodiment of the present invention.
Figure 10A:
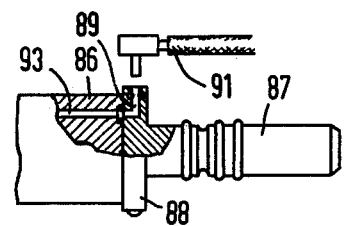

FIGS. 10a and 10b illustrate an embodiment of a handpiece in which both the first and second ports are located adjacent the coupling end of the center section to the handle section and these are between a cylindrical section 86 of the center section and a coupling shank 87. In this embodiment, the center section includes a removable coupling shank 87 which has a disk-shaped or flange portion 88 that serves as a distributor member. The coupling shank 87 will contain two passages 89 and 90 which are staggered by an angular amount. The first passage 89 has a portion extending radially to a first port that is a peripheral opening on the flange portion 88 and can receive a hollow prong of a connection element or distributor element of an exposed hose 91. The second portion 90 is in communication with a second passageway 92 that leads to the second port on the shank 87. When using one of the two types of handle sections, the desired one of the passageways 89 and 90 is positioned to be in communication with a fluid passageway 93 in the center section which passageway 93 extends to a source of cooling fluid.

The coupling shank 87 can be mounted by screws on the center section 86 in either a portion (FIG. 10a) to align the portions 89 and connect the first port with a passageway 93 in the center section or the position (FIG. 10b) to align port 90 with passage 93 connected to the second port. The screw hole spacing is selected to provide the desired amount of offset between the two positions. While the shank 87 is illustrated as being mounted by screws so that either the portion 89 or 90 are selectively in communication with the passageway 93, it may be constructed so that the shank 87 can be operatively switched over to position the desired portion 89 and 90 in communication with passageway 93. For this purpose, a guide pin would be provided and received in an elongated slot or groove. It is also conceivable to attach the coupling shaft 87 onto the frontal end of the handpiece section 86 by means of a rough cast bushing shell or socket.

Finally, it is conceivable to provide two different coupling shanks each of which has only one of the two channels 89 and 90. For example one contains a cooling agent channel 89 and the other will contain a cooling agent channel 90. Depending on the desire of the customer, one or the other of the two coupling shanks can be mounted on the section 86. However, this solution is only recommended if the customer only has one type of handle section which all have the same type of cooling agent supply means in his possession.

It is also conceivable to use a push button 94 which has been provided as a release for the handle section as a limiting stop for rotational movement of the coupling shank on the center section. If the center section 86 is provided with a corresponding slot that will coact with the notched button 94, rotational movement of the shaft portion 87 on the center section 86 will only occur when the notched button 94 is depressed.

Although various minor modifications may be suggested by those versed in the art, it should be understood that we wish to employ within the scope of the patent warranted hereon, all such modifications as reasonably and properly come within the scope of our contribution to the art.

We claim:

1. In a hand-held dental device including
a handpiece having a center section,
a drive means in said center section,
said handpiece being adapted to engage one of two different handle sections, each said handle section being demountably connectable at a rear end thereof to a forward end of said center section, each said handle section further having
  tool connection means at a forward working end thereof
  a drivable shaft means rotatably supported therein and extending therethrough between said drive means and said tool connection means,
  discharge nozzle means directed externally towards a dental tool positioned in said tool connection means, and
  pathway means for conducting cooling agent to said nozzle means, one of said handle sections having external such passageway means, the other having internal such passageway means, and
flexible supply hose means terminably functionally associated with said handpiece opposite said center section and containing longitudinally extending therein both energy supply line means for said drive means, and also tube supply means for said cooling agent,
the improvement which comprises in combination:
(A) conduit means functionally connected to said cooling agent tube means and longitudinally defined internally through said handpiece to internal port means defined in a forward end portion of said center section and adapted for making functional engagement with said pathway means when said pathway means is internally contained in said handle section,
(B) a bypass passageway means extending from said conduit means to external port means defined in said handpiece, said port means being adapted for making functional engagement with said pathway means when said pathway means is external of said handle section,
(C) selective connection means arranged to open said external port means and concurrently close said internal port means, and reversably and alternatively to close said external port means and concurrently open said internal port means,
whereby cooling fluid is alternatively deliverable to said discharge nozzle means by one of said conduit means and said bypass passageway.

2. The device of claim 1 wherein said connection means includes a tubular plug member telescopically extendable into said bypass passageway means through said external port means, a pair of resilient sealing members longitudinally spaced from one another along said bypass passageway for normally sealing said bypass passageway means and positioned for radially adjacent sealing relationship to said tubular plug member when such is extended into said bypass passageway means, said tubular plug member being adapted for connection to said pathway means externally of said handle section, said conduit means joining said bypass passageway means intermediately between said pair of sealing members.

3. The device of claim 1 wherein said connection means includes a ring member circumferentially extending about said handpiece about the region of said external port means and movable with respect to said handpiece between respective first and second positions, said ring member having channel means defined therein and ring port means defined in an outer position thereof which is joined to said ring channel means, the relationship between said port means, said ring member, said handpiece, and said ring channel means being such that when said ring member is in such first position said external port means is connected to said ring port means and when said ring member is in such second position said internal port means is connected therethrough to said conduit means.

4. The device of claim 1 wherein said connection means includes a check valve disposed internally in said handpiece and having spring means normally biasing said check valve into a position closing said external port means, and a tubular plug member telescopically extendable into said bypass passageway means through said external port means, said tubular plug member when so extended holding said check valve in a position opening said external port means, so that, when said check valve is in such closed portion, said internal port means connects through said conduit means, and, when said check valve is in such opened position, said external port means connects said conduit means via said bypass passageway means.

* * * * *